(12) United States Patent
Häring et al.

(10) Patent No.: US 7,906,596 B2
(45) Date of Patent: Mar. 15, 2011

(54) PROCESSES FOR ENZYMATIC SYNTHESIS OF POLY(OXYALKYLENE)ACRYLAMIDES

(75) Inventors: Dietmar Häring, Schriesheim (DE); Bernhard Hauer, Fussgönheim (DE); Stefan Becker, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 11/912,203

(22) PCT Filed: Apr. 20, 2006

(86) PCT No.: PCT/EP2006/061716
§ 371 (c)(1),
(2), (4) Date: Oct. 22, 2007

(87) PCT Pub. No.: WO2006/111566
PCT Pub. Date: Oct. 26, 2006

(65) Prior Publication Data
US 2008/0194767 A1    Aug. 14, 2008

(30) Foreign Application Priority Data
Apr. 22, 2005   (DE) .......................... 10 2005 018 935

(51) Int. Cl.
*C12P 13/02*   (2006.01)
(52) U.S. Cl. ......... 525/533; 435/128; 435/197; 435/129; 564/135; 525/8
(58) Field of Classification Search .................. 435/129, 435/197, 128; 564/135; 525/8, 533
See application file for complete search history.

(56) References Cited

U.S. PATENT DOCUMENTS

| 5,567,422 A | 10/1996 | Greenwald |
| 5,973,203 A * | 10/1999 | Egraz et al. .................... 564/135 |
| 2002/0022585 A1 * | 2/2002 | Morelli et al. ................ 510/475 |

FOREIGN PATENT DOCUMENTS

GB    2102426    2/1983

OTHER PUBLICATIONS

Jeffamine M-1000 Technical Bulletin.*
Website of "The Jeffamine Polyetheramine" from "http://www.huntsman.com/performance_products/Media/JEFFAMINE_Polyetheramines.pdf" (2007).*
Jeffamine M-1000 Technical Bulletin (2007).*
Sánchez, V., et al., "Highly efficient enzymatic ammonolysis of $\alpha,\beta$-unsaturated esters", Synlett, 1994, pp. 529-530.
Puertas, S., et al., "Lipase catalyzed aminolysis of ethyl propiolate and acrylic esters. Synthesis of chiral acrylamides", Tetrahedron, 1993, vol. 49, No. 19, pp. 4007-4014.
Margolin, A. L., et al., "Chemoenzymatic synthesis of optically active (meth)acrylic polymers", J. Am. Chem. Soc., 1991, vol. 113, pp. 4693-4694.

* cited by examiner

*Primary Examiner* — Vasu Jagannathan
*Assistant Examiner* — Mark S Kaucher
(74) *Attorney, Agent, or Firm* — Connolly Bove Lodge & Hutz LLP

(57) ABSTRACT

Processes for enzymatic synthesis comprising: (a) providing an aliphatic poly(oxyalkylene)amine; and (b) reacting the aliphatic poly(oxyalkylene)amine with a reactant selected from the group consisting of acrylic acid compounds and alkyl esters thereof, in the presence of a hydrolase in bulk or in a liquid reaction medium comprising an organic solvent to for a poly(oxyalkylene)acrylamide.

11 Claims, No Drawings

PROCESSES FOR ENZYMATIC SYNTHESIS OF POLY(OXYALKYLENE)ACRYLAMIDES

CROSS-REFERENCE TO RELATED APPLICATIONS

This application is a national stage application, under 35 U.S.C. §371, of PCT/EP2006/061716, filed Apr. 20, 2006, which claims priority of German Application No. 10 2005 018 935.0, filed Apr. 22, 2005.

BACKGROUND OF THE INVENTION

The poly(oxyalkylene)acrylamides are obtainable by various routes. The chemical synthesis of poly(oxyalkylene)acrylamides is effected by direct esterification or transesterification of acrylic acid or acrylic esters with poly(oxyalkylene) amines and proceeds at temperatures of above 100° C. under acid catalysis (DE 3130508 Röhm GmbH 1981).

Owing to the high temperatures, the addition of large amounts of polymerization inhibitors is necessary. As a result of the high reaction temperatures, Michael adducts of the amine to the double bond of the acrylic acid compound form. Complex and often dark product mixtures with troublesome odor are formed. The reaction of acryloyl chloride with amines likewise affords N-alkylacrylamides. However, the process is not economically viable owing to the high costs of acryloyl chloride.

The biocatalytic synthesis of acrylamides is described in the documents which follow. Puertas et al. (Tetrahedron 1993, 49, 4007-4014) describe the reaction of methyl (meth)acrylate with butylamine, benzylamine, 2-aminobutane and 2-aminoheptane. The lipase-catalyzed syntheses gave rise to yields of 40-95% within 3-10 days.

Sanchez et al. (Synlett 1994, 529-530) describe the ammonolysis of methyl(meth)acrylate with ammonia to give (meth)acrylamide. The lipase-catalyzed reaction afforded up to 91% yield after 93 h.

Margolin et al. (J. Am. Chem. Soc. 1991, 113, 4693-4694) describe the reaction of trifluoroethyl methacrylate with 1-(1-naphtyl)ethylamine or phenylalaninamide. The reaction was catalyzed by the protease subtilisin.

Egraz et al. (U.S. Pat. No. 5,973,203) claim the enzymatic synthesis of (meth)acrylamides comprising tertiary amino groups. In this synthesis, an alkyl(meth)acrylate reacts with a diamine which has one primary and one tertiary amino group.

BRIEF SUMMARY OF THE INVENTION

It was therefore an object of the invention to develop a process for preparing poly(oxyalkylene)acrylamide. The synthesis should in particular enable the preparation of poly(oxyalkylene)acrylamides in high purity and good yield, and suppress the occurrence of undesired side reactions.

The invention relates to a process for enzymatically synthesizing poly(oxyalkylene)acrylamides and to a process for preparing polymeric poly(oxyalkylene)acrylamides, to the polymers obtainable by this process and to their use.

The invention firstly relates to a process for enzymatically synthesizing poly(oxyalkylene)acrylamide, wherein an aliphatic poly(oxyalkylene)amine is reacted in the presence of a hydrolase in bulk or in a liquid reaction medium comprising an organic solvent with an acrylic acid compound or an alkyl ester thereof, and the poly(oxyalkylene)acrylamide(s) formed is/are isolated if appropriate from the reaction mixture after the reaction has ended.

DETAILED DESCRIPTION OF THE INVENTION

In the context of the invention, an "aliphatic poly(oxyalkylene)acrylamide" is mono- or polyacrylated.

The conversion achieved in accordance with the invention (molar fraction of poly(oxyalkylene)acrylamide which bears at least one amide group) is, according to the invention, at least 20 mol %, for example from 20 to 100 mol %, from 40 to 99 mol %, from 50 to 95 mol % or from 75 to 95 mol %, based in each case on the moles of poly(oxyalkylene)amine used.

The liquid organic reaction medium may have an initial water content of up to about 10% by volume, but is preferably substantially anhydrous. The reaction may be effected in bulk or, if advantageous, also after addition of a suitable organic solvent.

The organic solvents used with preference are those selected from tert-butanol and tert-amyl alcohol, pyridine, poly-$C_1$-$C_4$-alkylene glycol di-$C_1$-$C_4$-alkyl ethers, in particular polyethylene glycol di-$C_1$-$C_4$-alkyl ether, for example dimethoxyethane, diethylene glycol dimethyl ether, polyethylene glycol dimethyl ether 500, tert-butyl acetic ester, MTBE, acetone, 1,4-dioxane, 1,3-dioxolane, THF, dimethoxymethane, dimethoxyethane, cyclohexane, methylcyclohexane, toluene, hexane and their monophasic or multiphasic mixtures.

In the process according to the invention, acrylic acid compound and poly(oxyalkylene)amine are used generally in a molar ratio of from about 100:1 to 1:1, for example in the range from 30:1 to 3:1 or from 10:1 to 5:1.

The initial poly(oxyalkylene)amine concentration is, for example, in the range from about 0.1 to 20 mol/l, in particular from 0.15 to 10 mol/l.

The poly(oxyalkylene)amine is preferably selected from polyoxyalkyleneamines, preferably polyoxyethyleneamines and polyoxypropyleneamines or mixed polyoxyethylene-propyleneamines, having 1-250, preferably 2-100, more preferably 3-50, oxyalkylene units and at least one, preferably exactly one, terminal amino function.

The poly(oxyalkylene)amines ("polyetheramines") are prepared by alkoxylating alcohols and subsequently aminating with ammonia, as described, for example, in WO 01/98388. They are also commercially available, for example from BASF or Huntsman ("Jeffamine"®).

The "acrylic acid compound" used in accordance with the invention is preferably selected from acrylic acid, methacrylic acid, their anhydrides, lower alkyl-substituted, i.e. $C_1$-$C_6$-alkyl-substituted (meth)acrylic acid, the $C_1$-$C_{20}$-alkyl esters thereof or ethylene glycol diacrylates; and also mixtures of these compounds. Preferred $C_1$-$C_6$-alkyl groups are in particular methyl or ethyl groups. Preferred $C_1$-$C_{20}$-alkyl groups are, for example, methyl, ethyl, i- or n-propyl, n-, i-, sec- or tert-butyl, n- or i-pentyl; and also n-hexyl, n-heptyl, n-octyl, n-nonyl, n-decyl, n-undecyl, n-tridecyl, n-tetradecyl, n-pentadecyl and n-hexadecyl, and n-octadecyl, and also the mono- or polybranched analogs thereof. Preference is given to using (meth)acrylic acid or (meth)acrylic acid derivatives.

Suitable derivatives of the above acrylic acid compounds, for example acrylic acid and methacrylic acid, are esters with saturated and unsaturated, cyclic or open-chain $C_1$-$C_{10}$-monoalcohols, in particular the methyl, ethyl, butyl and 2-ethylhexyl esters thereof. The inventive $C_1$-$C_{10}$-monoalcohols comprise preferably $C_1$-$C_6$-alkyl groups of the above definition or their longer-chain, optionally branched homologs having up to 10 carbon atoms or $C_4$-$C_6$-cycloalkyl groups such as cyclopropyl, cyclopentyl or cyclohexyl, each of which may be optionally substituted by one or more alkyl groups having from 1 to 3 carbon atoms.

When no other information is given, $C_1$-$C_6$-alkyl represents, according to the invention, methyl, ethyl, n- or i-propyl, n-, sec- or tert-butyl; n- or tert-amyl, and also straight-chain or branched hexyl. $C_3$-$C_6$-Alkyl is in particular n- or i-propyl, n-, sec- or tert-butyl, n- or tert-amyl, and also straight-chain or branched hexyl. $C_1$-$C_4$-Alkylene is preferably methylene, ethylene, propylene or 1- or 2-butylene.

The hydrolases used in accordance with the invention are selected from esterases (E.C. 3.1.-.-), in particular lipases (E.C. 3.1.1.3), glycosylases (E.C. 3.2.-.-) and proteases (E.C. 3.4.-.-) in free or immobilized form. Particularly suitable enzymes are Novozyme 435 (Lipase from *Candida Antarctica* B) or lipase from *Aspergillus* sp., *Burkholderia* sp., *Candida* sp., *Pseudomonas* sp., or *porcine* pancreas.

The enzyme content in the reaction medium is in particular in the range from about 0.1 to 10% by weight based on the polyol used. The enzymes may be used in the reaction according to the invention in pure or supported (immobilized) form.

The process according to the invention is preferably carried out in such a way that the reaction temperature is in the range from 0 to about 100° C., in particular in the range from 20 to 80° C. The reaction time is usually in the range from about 1 to 72 hours, preferably 6-24 hours.

The alcohol which is obtained in the reaction if appropriate (generally a monohydric alcohol, for example methanol or ethanol) or the water of reaction obtained in the amidation may, if necessary, be removed in a suitable manner from the reaction equilibrium, continuously or stepwise. Suitable for this purpose are preferably molecular sieves (pore size, for example, 3-10 ångstrøm), or removal by distillation, by means of suitable semipermeable membranes or by pervaporation.

To mix the reaction mixture, any methods may be used. Specific stirrer apparatus is not required. The reaction medium may be monophasic or multiphasic and the reactants are dissolved, suspended or emulsified therein, initially charged together with the molecular sieve if appropriate. To start the reaction, the medium may be admixed with the enzyme preparation. The temperature is adjusted to the desired value during the reaction.

Alternatively, the reaction may also be carried out in such a way that the enzyme is initially charged in immobilized form in a fixed bed reactor and the reaction mixture is pumped through the immobilized enzyme, if appropriate in circulation. Water of reaction and/or alcohol may likewise be removed continuously or stepwise from the reaction mixture.

The process according to the invention may be carried out batchwise, semicontinuously or continuously in conventional reactors (for example stirred tanks, fixed bed reactors).

After the reaction has ended, the desired poly(oxyalkylene)acrylamide can be isolated from the reaction mixture, for example chromatographically purified, and then used to prepared the desired polymers or copolymers. The reaction mixture may also be reused directly after removal of the enzyme (filtration, decantation).

The invention further relates to a process for preparing polymeric poly(oxyalkylene)acrylamides, wherein at least one poly(oxyalkylene)acrylamide is prepared in the above manner; the poly(oxyalkylene)acrylamide is removed from the reaction mixture if appropriate; and polymerized, if appropriate together with further comonomers.

Suitable further comonomers are: other poly(oxyalkylene) acrylamides of the inventive type prepared in accordance with the invention or polymerizable monomers such as (meth) acrylic acid, (meth)acrylic esters, maleic acid, itaconic acid, their alkali metal or ammonium salts and their esters, O-vinyl esters of $C_1$-$C_{25}$-carboxylic acids, N-vinylamides of $C_1$-$C_{25}$-carboxylic acids, N-vinylpyrrolidone, N-vinylcaprolactam, N-vinyloxazolidone, N-vinylimidazole, quaternized N-vinylimidazole, (meth)acrylonitrile, ethylene, propylene, butylene, butadiene, styrene. Examples of suitable $C_1$-$C_{25}$-carboxylic acids are saturated acids such as formic acid, acetic acid, propionic acid and n- and i-butyric acid, n- and i-valeric acid, caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachic acid, behenic acid, lignoceric acid, cerotic acid and melissic acid.

Such polymers are prepared, for example, in analogy to the processes described in general terms in "Ullmann's Encyclopedia of Industrial Chemistry, Sixth Edition, 2000, Electronic Release, heading: Polymerization Process". Preference is given to effecting the (co)polymerization as a free-radical polymerization in the form of solution, suspension, precipitation or emulsion polymerization, or by polymerization in bulk, i.e. without solvent.

Such polymers are prepared under metal catalysis without alkaline ester cleavage, as described, for example, in U.S. Pat. No. 6,359,101, DE 198 17 676, DE 199 13 260, U.S. Pat. No. 6,429,342, U.S. Pat. No. 6,077,979 and U.S. Pat. No. 5,545,601.

The invention further relates to the use of the inventive poly(oxyalkylene)acrylamides for producing concrete plasticizers or dispersants.

Experimental Section

The following poly(oxyalkylene)amines were used:

"Polyetheramine 520": Polyethylene glycol amine monomethyl ether (approx. 520 g/mol)

"Polyetheramine 750": Polyethylene glycol amine monomethyl ether (approx. 750 g/mol)

EXAMPLE 1

Preparation of Poly(Oxyalkylene)Acrylamide (Variation of the Reactant Ratio)

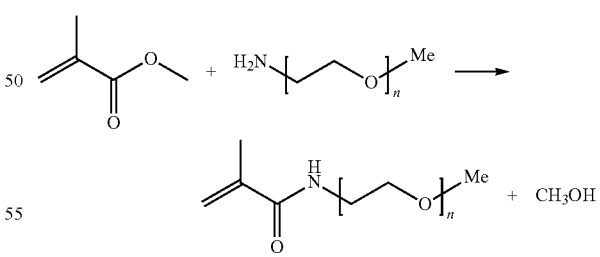

5 mmol of polyetheramine 750 (3.75 g), 25 or 50 mmol of methyl methacrylate (MMA), if appropriate 1.0 g of molecular sieve (5 A) and 200 mg of Novozyme 435 (supported lipase from *Candida Antarctica* from Novozymes, Denmark) were stirred at 60° C. over 24 h. The enzyme was filtered off and washed with a little methyl tert-butyl ether, and the excess MMA and MTBE were removed on a rotary evaporator under reduced pressure. The conversion depended upon the methyl methacrylate excess, as the following table shows.

| Molar amine/MMA ratio | Conversion [%] without molecular sieve | Conversion [%] with molecular sieve |
|---|---|---|
| 1/10 | 98 | 98 |
| 1/5 | 83 | 84 |

Product Analysis

In the H NMR analysis in $CD_3OD_3$, the signal of the "amine reactant" at 2.75 ppm ($CH_2$—$NH_2$) disappears and a new "amide signal" at 3.43 ppm ($\overline{CONH}$—$CH_2$) appears. The conversion was calculated as follows via the integrals: (amide*100%)/(amide+amine).

EXAMPLE 2

Addition of Methacrylic Acid 5 mmol of polyetheramine 520 (2.6 g), 50 mmol of methyl methacrylate (MMA), if appropriate 1.0 g of molecular sieve (5 A), varying amounts of methacrylic acid (MA) and 200 mg of Novozyme 435 (supported lipase from *Candida Antarctica* from Novozymes, Denmark) were stirred at 20° C. over 24 h. The enzyme was filtered off and washed with a little methyl tert-butyl ether, and the excess MMA and MTBE were removed on a rotary evaporator under reduced pressure. The conversion depended upon the methacrylic acid addition, as the following table shows.

| Methacrylic acid [mmol] | Conversion [%] without molecular sieve | Conversion [%] with molecular sieve |
|---|---|---|
| 0 | 77 | 79 |
| 0.05 | 78 | 79 |
| 0.5 | 100 | 96 |

EXAMPLE 3

Preparative Reaction 0.25 mol of polyetheramine 750 (187.5 g), 2.5 mol of methyl methacrylate (250 g) and 10.0 g of Novozyme 435 (supported lipase from *Candida Antarctica* from Novozymes, Denmark) were stirred at 60° C. over 24 h. The enzyme was filtered off with suction through a suction filter and washed with a little methyl tert-butyl ether, and the excess methyl methacrylate and MTBE were removed on a rotary evaporator under reduced pressure. 183 g of a clear pale yellowish oil were obtained and were polymerizable without further workup. A conversion of >99% was achieved.

EXAMPLE 4

Preparative Reaction 52.0 g of polyetheramine 520 (0.1 mol), 100.1 g of methyl methacrylate (1.0 mol) and 4.0 g of Novozyme 435 were stirred at 40° C. For workup, the supported enzyme was filtered off with suction through a suction filter and washed with a little MTBE, and excess solvents and MMA were removed on a rotary evaporator under reduced pressure. 55.6 g of a colorless liquid were obtained. According to H NMR analysis, the amine had reacted with MMA to an extent of 95%.

What is claimed is:

1. A process comprising:
   (a) providing an aliphatic poly(oxyalkylene)amine having exactly one terminal amino function; and
   (b) reacting the aliphatic poly(oxyalkylene)amine with a reactant selected from the group consisting of acrylic acid compounds and alkyl esters thereof, in the presence of a hydrolase in bulk or in a liquid reaction medium comprising an organic solvent to form a poly(oxyalkylene)acrylamide.

2. The process according to claim 1, further comprising isolating the poly(oxyalkylene)acrylamide.

3. The process according to claim 1, wherein the liquid reaction medium has an initial water content of less than about 10% by volume.

4. The process according to claim 1, wherein the reactant and the poly(oxyalkylene)amine are reacted in a molar ratio of about 100:1 to 1:1.

5. The process according to claim 1, wherein the reactant comprises at least one selected from the group consisting of acrylic acid, lower alkyl-substituted acrylic acid, the alkyl esters thereof, and mixtures thereof.

6. The process according to claim 1, wherein the hydrolase comprises a lipase.

7. The process according to claim 1, wherein the poly(oxyalkylene)amine has a molar mass of 500 to 10 000 g/mol.

8. The process according to claim 1, wherein the hydrolase is present in the reaction in an amount of about 0.01 to 10% by weight based on the poly(oxyalkylene)amine.

9. The process according to claim 1, wherein the reaction is carried out at a temperature of 0 to about 100° C.

10. The process according to claim 1, wherein the reaction medium is monophasic or multiphasic and the poly(oxyalkylene)amine and the reactant are dissolved, suspended or emulsified therein.

11. The process according to claim 1, wherein alcohol or water of reaction formed during the reaction is removed.

* * * * *